United States Patent [19]

Muetterties

[11] 4,173,222

[45] Nov. 6, 1979

[54] APPARATUS FOR CONTROLLABLY ADMINISTERING A PARENTERAL FLUID

[75] Inventor: Andrew J. Muetterties, Gages Lake, Ill.

[73] Assignee: Abbott Laboratories, North Chicago, Ill.

[21] Appl. No.: 715,810

[22] Filed: Aug. 19, 1976

[51] Int. Cl.² ............................................. A61M 5/16
[52] U.S. Cl. ............................ 128/214 C; 128/214.2;
222/67; 222/481; 137/179; 137/192; 137/399; 137/590
[58] Field of Search ........... 128/214 R, 214 C, 214 E,
128/214.2, 227, 214 D; 222/22, 52, 67, 145, 481;
137/179, 192, 399, 590

[56] References Cited

U.S. PATENT DOCUMENTS

| 3,216,419 | 11/1965 | Scislowicz | 128/214 C |
| 3,217,711 | 11/1965 | Pecina et al. | 128/214 R |
| 3,738,361 | 6/1973 | Price | 128/214 E |
| 3,999,542 | 12/1976 | Shaw | 128/214 E X |

FOREIGN PATENT DOCUMENTS

| 977039 | 12/1964 | United Kingdom | 128/214 C |
| 1182016 | 2/1970 | United Kingdom | 128/214 C |

*Primary Examiner*—Dalton L. Truluck
*Attorney, Agent, or Firm*—Robert L. Niblack; Neil E. Hamilton

[57] ABSTRACT

An apparatus for administering parenteral liquids from a parenteral fluid container which provides a sufficient quantity of parenteral liquid to be administered at a slower than normal rate so as to afford a keep-vein-open (KVO) means. The apparatus utilizes a first orifice to afford a faster flow rate than a second orifice spaced away from the first orifice. The preferred means for regulating different flow rates of fluid through the two orifices are the dimensions of the orifices and filters having different mesh sizes. When the parenteral liquid is maintained in the reservoir in contact with the first orifice with the faster flow rate, liquid will pass through both orifices at a predetermined regular rate. When liquid no longer contacts the first orifice, as when the fluid container is depleted of liquid, the second orifice then comes into effect to afford a slower rate of liquid until a new container can be supplied.

31 Claims, 9 Drawing Figures

APPARATUS FOR CONTROLLABLY ADMINISTERING A PARENTERAL FLUID

BACKGROUND OF THE INVENTION

This invention relates to an apparatus which can controllably administer a parenteral liquid. More particularly, this invention relates to an intravenous administration set which will revert to a different or keep-vein-open (KVO) flow rate when the solution in a container empties.

In the administration of parenteral liquids, the source of parenteral liquid will eventually be exhausted. Unless a constant surveillance is made during the administration, in many instances the source of liquid will become depleted to the patient with the needle in communication wtih the vein. When this occurs, blood can coagulate around the needle thus effecting a blockage of the end of the needle or the situs where the needle enters the vein. In order to then effect flow when a new solution container is attached, the needle would have to be withdrawn and reinserted at a new site. A unit which is provided to obviate the foregoing adverse effects and to afford a different flow rate in a parenteral liquid is described by Price in U.S. Pat. No. 3,738,361. However, this particular unit requires precise positioning of moving parts which is costly to manufacture and can cause problems during usage.

It is an advantage of the present invention to provide a novel administration apparatus for a parenteral liquid which has a keep-vein-open means. Other advantages are an apparatus for administering I.V. liquids which affords two different flow rates with means which are easy to fabricate and afford positive and reliable functions; an I.V. administration unit which not only can afford different flow rates but can do so without utilizing moving parts or in some instances with a minimum of moving parts; an apparatus which can accomplish a keep-vein-open effect without moving parts and which affords an added advantage of filtering out particulate matter as well as air or gases; a device which in certain embodiments will retain a level of I.V. liquid in the sight chamber and tubing even when the KVO reservoir empties thus avoiding a new venipuncture.

SUMMARY OF THE INVENTION

The foregoing advantages are accomplished and the shortcomings of the prior art overcome by the present apparatus which is comprised of a reservoir chamber having connection means for a fluid container. The connection means defines a fluid flow inlet passageway into the chaamber and closure means are in fluid tight engagement with the opposing end of the chamber to define a fluid flow outlet passageway. Fluid passage means extend into the chamber and in communication with the fluid flow outlet passageway. Two separate orifices are in communication with the fluid passage means with the orifices spaced from each other a predetermined distance. In some embodiments the first orifice is positioned closer to the inlet passageway with the second orifice closer to the outlet passageway. In another embodiment, the two orifices are disposed at the same level and are equidistance from the inlet and outlet passageways. Means are operatively associated with the first and second orifices to provide a flow rate through the combined first and second orifices which is faster than the flow rate through the second orifice alone and to substantially eliminate the flow of air into said first orifice. The usual length of tubing is connected to the closure means defining the outlet passage for administering the liquid to the patient.

In a preferred embodiment, the means for affording the different flow rates through the two orifices are filter means having different mesh sizes. In other embodiments, a captive float valve is positioned in conjunction with an orifice of a predetermined size which will seal the orifice when the liquid level passes below it. The second orifice can either compose a filtered inlet of predetermined size or a valve member which can be set to a predetermined size. If desired, an orifice closer to the outlet passage can be left unfiltered. Further, the connection means to the reservoir having the fluid passage means with the two spaced orifices, can be a piercing pin either of the vented or nonvented type.

BRIEF DESCRIPTION OF THE DRAWINGS

A better understanding of the apparatus for administering a parenteral liquid according to this invention will be accomplished by reference to the drawings wherein.

DESCRIPTION OF ONE EMBODIMENT

Figure 1:
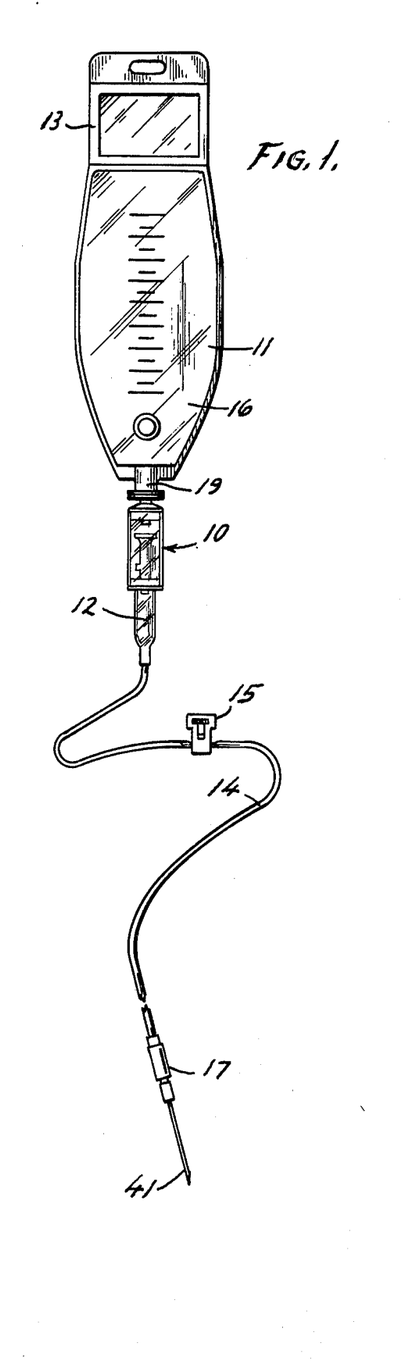
FIG. 1 is a view in side elevation showing the apparatus of this invention operatively connected to an I.V. solution bag and having interconnected thereto the usual tubing with a needle and control clamp.

Proceeding to a detailed description of one embodiment of the present invention, the controlled I.V. administration apparatus 10 is shown in FIG. 1 in conjunction with a conventional parenteral solution bag 11 which is described in U.S. Pat. No. 3,915,212. A standard drip or sight chamber 12 is secured to the opposite end of the I.V. administration apparatus and a length of tubing 14 extends from the drip chamber which is ultimately connected to a needle assembly 17 with the control of fluid in the tubing being effected by means of an adjustable type clamp 15.

Figure 2:
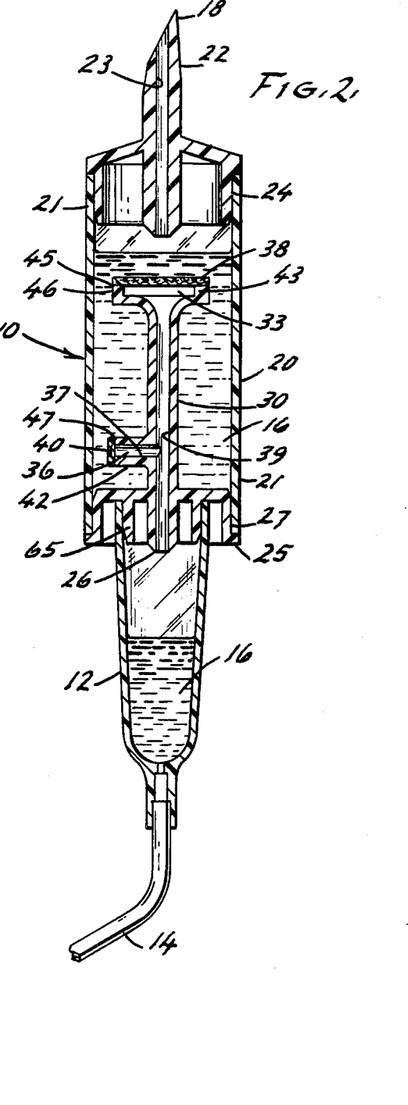
FIG. 2 is a view in vertical section of the apparatus of this invention showing the reservoir filled to an operative level with liquid and the two orifices spaced from each other in the reservoir as well as a drip chamber integrally secured at the bottom of the reservoir.

As best seen in FIG. 2, the control I.V. administration apparatus 10 is composed of a reservoir chamber 20 having a flexible cylindrical side wall 21. Enclosing one end of the chamber is a piercing pin assembly 22 having a pointed end portion 18 and a reduced diameter section 24 for accommodating side wall 21. A fluid flow inlet passageway 23 extends through the piercing pin assembly to permit I.V. liquid to flow into chamber 20. At the opposite end of chamber 20, is a closure 25 having a reduced diameter section 27 for accommodating wall 21 and also a centrally disposed drip forming member 26. Extending from the drip forming member 26 and as a continuation thereof is a horn-like, tubular, fluid passage means 30 having at one end a first orifice 33 adjacent the inner end of inlet passageway 23 and a spaced second orifice 36. It will be noted that the first orifice 33 is in effect formed from an enlarged diameter section 43 having an annular section 46 with a flat wall 45 for seating of the filter 38 and securing it thereto such as by means of heat sealing. Alternatively, ultrasonic or epoxy sealing could be used. Similarly, filter means 40 is secured to the end of orifice 36 formed from tubular member 42 also having a flat end wall 47 for securing the filter to it. Preferably, filters 38 and 40 are formed from a cellulose acetate material and are produced by the Millipore Filter Corporation located at Bedford, Mass. or Sartorius-Membranfilter GMBH located at Weender Landstr, West Germany. The filter materials are of the hydrophilic type. In the instance of filter 38, it is of 0.8 of micron size and is 0.75 inches in diameter whereas filter membrane 40 is 0.22 microns and is 0.25 inches in diameter.

Orifice 33 has an internal diameter of 0.55 inches as measured by the internal diameter of section 46 whereas orifice 36 has a diameter of 0.10 inches as measured by the internal diameter of tubular member 42 forming channel 37. The internal diameter of fluid passage means 30 forming channel 39 is from 0.152 inches to 0.210 inches.

Extending from closure 25 and secured thereto by means of annular flange 65, is a standard cylindrical drip chamber 12 which has secured at the opposing end a length of flexible plastic tubing 14 for delivery of I.V. liquid 16.

DESCRIPTION OF OTHER EMBODIMENTS

In the following FIGS. 3–9, other embodiments of the previously described controlled I.V. administration apparatus 10 are described. Similar parts will be referred to with similar numbers except they will be in the "100", "200", "300", "400", "500", "600" or "700" series. The same dimensions will apply concerning previously indicated orifice and tubular sizes, except where stated.

Figure 3:
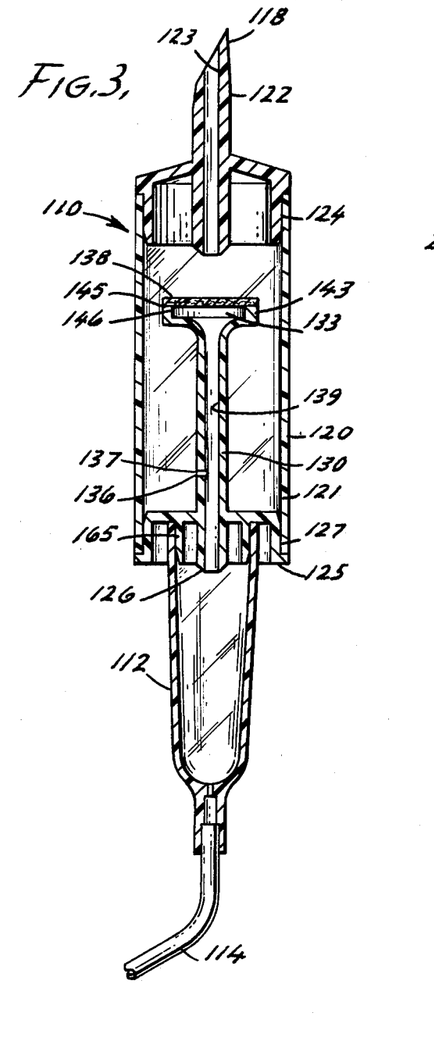
FIG. 3 is a view similar to FIG. 2 showing an alternative embodiment of the invention.

In the embodiment shown in FIG. 3, controlled I.V. administration apparatus 110 is substantially the same as for unit 10 except that the second orifice 136 does not have a tubular extension arm 42 or a filter means 40 secured to the end thereof. It instead has micron size or capillary passage 137 in tubular fluid passage means 130 which can be formed by a laser beam. The flow through passage 137 will be determined by the length as well as its size with the controlling factor being that the longer the passage the larger the diameter. In this particular embodiment, the faster flow rate through the first orifice 133 is effected by means of the porosity of the filter 138 and the size of the orifice 133 which is determined by the enlarged annular portion 146 when compared with the smaller orifice 136 and the smaller channel 137 extending laterially through the fluid passage means 130.

Figure 4:
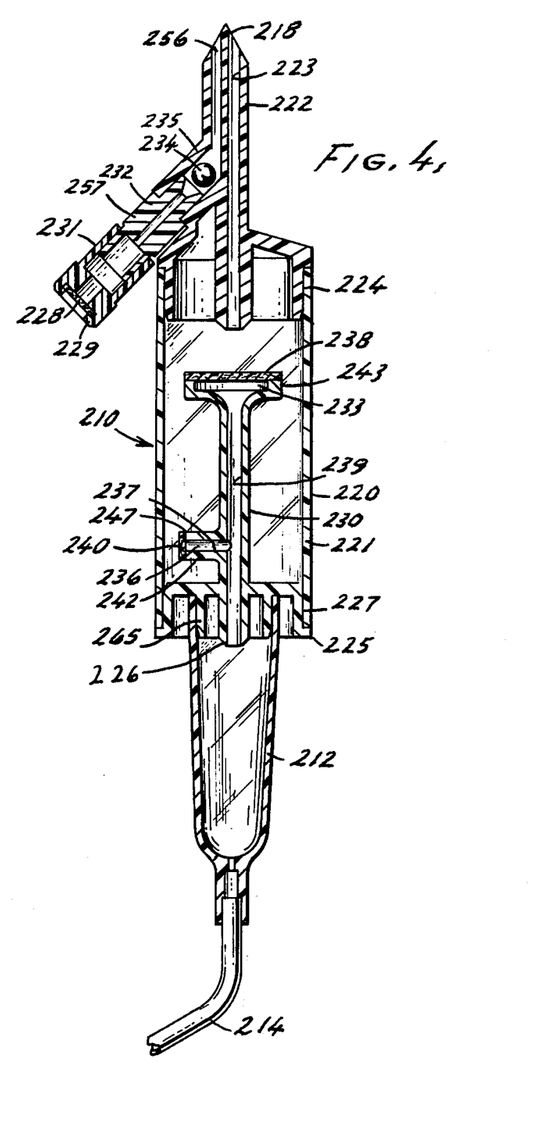
FIG. 4 is a view similar to FIG. 2 showing an additional alternative embodiment.

The embodiment illustrated in FIG. 4, with similar parts indicated in the "200" series, is basically the same as the unit 10 described in FIGS. 1 and 2 except that it includes in the piercing pin assembly 222 an air inlet passage 256 which is in communication with a combined filter and check valve assembly 257. The latter assembly is basically described in U.S. Pat. No. 3,157,481 which is commonly assigned. This embodiment is constructed for the purpose of withdrawing I.V. fluid from a rigid container such as a glass solution bottle with the air filter assembly 257 supplying air into the solution container. The combined filter and check valve 257 is composed of a ball check valve 234 which is captively held in side arm 235 by means of an intermediate tubular, valve seat member 232. Member 232 has interconnected at the opposing end, an air cap tubular member 231 with a filter material 228 which is held thereon by means of flange 229.

Figure 5:
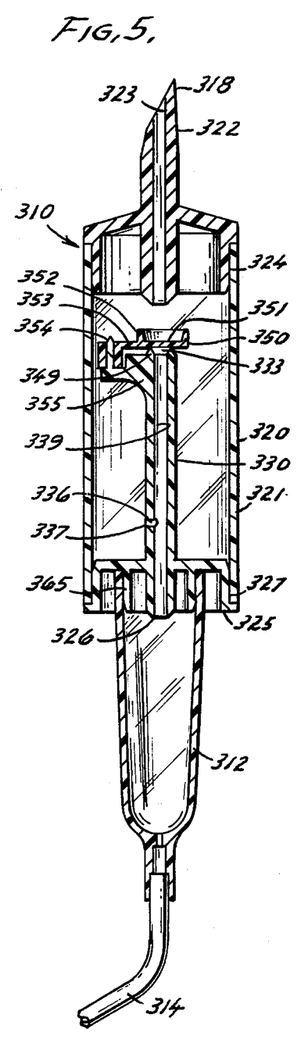
FIG. 5 is a view similar to FIG. 2 illustrating another embodiment.
Figure 6:
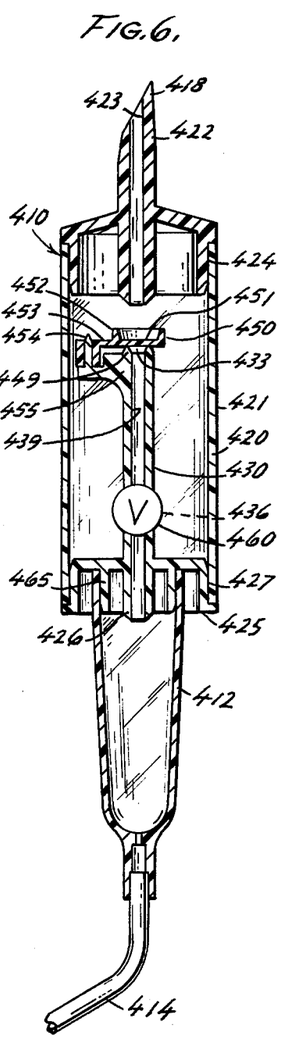
FIG. 6 is a view similar to FIG. 2 showing still another embodiment.
Figure 7:
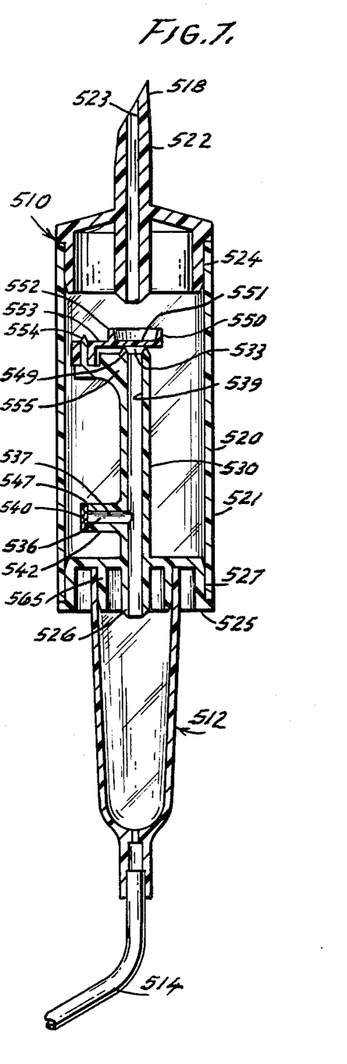
FIG. 7 is a view similar to FIG. 2 showing yet another embodiment.

In the embodiments described in FIGS. 5, 6 and 7 the single channel piercing pin assembly similar to that described at 22 and 122 is utilized but in place of the upper filter means as described in the previous embodiments a float-type valve such as 350, 450 and 550 is utilized in conjunction with the first orifices 333, 433 and 533. The float valve is basically the same as that described in U.S. Pat. No. 3,216,419 which is commonly assigned and is particularly shown in FIG. 5 of that patent. As the float valve is the same in all of the embodiments 310, 410 and 510, it will be described only in relation to unit 310 in FIG. 5. It will be noted that the float valve 350 is composed of a flexible diaphragm 351 which is surrounded by a retaining member 352 attached to a hinge member 353 which is secured on post 354 supported by lateral support 355 extending from the tubular passage means 330. In unit 310, it will be seen that the second orifice 336 is the same as previously described for orifice 136 in unit 110.

In embodiment 410, specifically described in FIG. 6, the float valve 450 is employed in conjunction with the first orifice 433 and the second orifice 436 is represented by a preset valve 460 which will be preset at a slower rate than the liquid flow through orifice 433.

In FIG. 7, embodiment 510 also utilizes the float valve 550 and a second orifice means similar to that described in unit 10. The second orifice means 536 utilizes a filter means 540 supported at the end of a laterally extending tubular means 542 having a flat wall 547.

Figure 8:
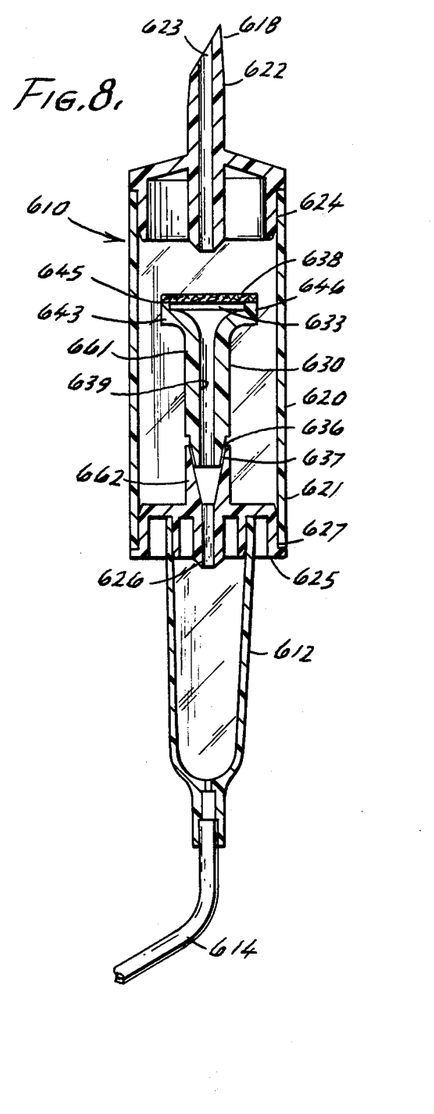
FIG. 8 is a view similar to FIG. 2 illustrating yet another embodiment.

The FIG. 8 embodiment 610 is somewhat similar to unit 110 except fluid passage means 630 is formed in two portions by upper passage means 661 and lower passage means 662 with the two portions joined in a standard Luer fitment. Second orifice 636 is formed in the Luer fitment by scratching the adjacent wall surface of portion 661 to form a capillary channel 637 therein.

Figure 9:
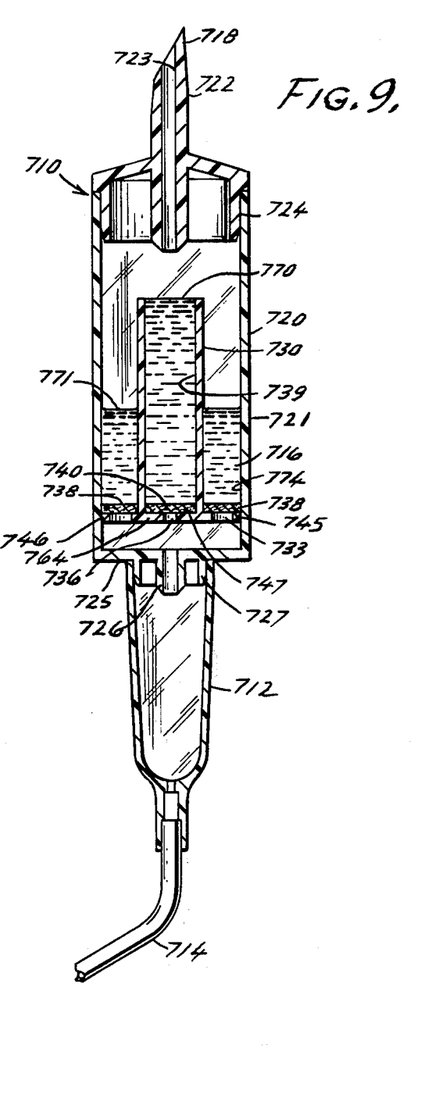
FIG. 9 is a view similar to FIG. 2 depicting still a further embodiment.

A double filter orifice is employed in unit 710 shown in FIG. 9. In this particular embodiment the first or faster flow rate orifice 733 is in part formed from an annular chamber disposed between the tubular fluid passage means 730 and the side wall 721 of reservoir chamber 720. A larger mesh filter 738 will be disposed between wall 721 and tubular member 730 with support from annular ledge portion 746 and flat wall 745. Further support is provided by T-shaped ledge 764 which also supports smaller mesh filter 740 at the end of tubular member 730 opposite its open end. Filter 740 will later be referred to in the Operation as the KVO filter. Suitable bridging portions (not shown) will interconnect annular portion 746 and ledge 764. In this particular embodiment, both orifices 733 and 736 are concentrically positioned with orifice 733 spaced outside the confines of tubular member 730.

OPERATION

A better understanding of the advantages of the controlled I.V. administration apparatus 10 as well as those described in the other embodiments will be had by description of their operation. As all of the units operate on basically the same principle, only the embodiment referred to as unit 10 will be described with specific comments made for the other embodiments in any manner in which they may differ in their operation.

The controlled I.V. administration apparatus 10 will be packaged separately from a solution container 11 and when it is desired to administer the contents of an I.V. liquid 16, such as contained in an I.V. bag 11, the piercing pin 18 will be inserted through the rubber reseal unit 19 to provide fluid communication between the inside of bag 11 and reservoir chamber 20. At this point, the unit 10 will be assembled as shown in FIG. 1 with bag 11 suitably supported in a vertical position. The reservoir chamber 20 will be primed by squeezing together the flexible side wall 21 as required to fill it so that the fluid passage means or reservoir core 30 is submerged and the chamber filled to a level of liquid 16 as shown in FIG. 2. The drip chamber 12 will next be primed by squeezing it wall to wall and held in a squeezed position until the tubing clamp 15 is closed. The force is then released on the drip chamber 12 which action will draw solution through the membranes 38 and 40 and prime the drip chamber. The foregoing action can be repeated as needed to fill the drip chamber 12 half full as indicated in FIG. 2.

After the foregoing priming operation, the needle assembly 17 is attached and the air in tubing 14 is expelled by opening the clamp and allowing the set to run. The appropriate venipuncture is made by needle 41 and the set which includes all of the foregoing mentioned components in conjunction with the controlled I.V. administration apparatus 10 is then ready for I.V. administration. Fluid 16 flow rate is established by adjusting the flow clamp 15 until the desired rate of administration is obtained. Liquid will continue to flow through both orifices 33 and 36 across their respective filter means 38 and 40 with a faster flow being accomplished across filter 38 due to its larger mesh size and the larger size of orifice 33. Fluid will continue to be administered at a given predetermined rate with flow through both orifices 33 and 36 and out of outlet passageway 26 until the solution container empties. When this occurs, the fluid level in the reservoir 20 will drop below the level of the larger upper hydrophilic membrane 38. At this point, the controlled I.V. administration apparatus 10 will revert to a keep-vein-open rate which will be a slower one than that accomplished in utilizing both the upper and lower orifices 33 and 36, respectively. Once the level is below the upper orifice 33, all the liquid flow will be through the second orifice 36 and across filter 40 which will be at a much slower rate than for both. This slower rate is established so that a constant flow is permitted through drip chamber 12, tubing 14 and into the vein so as to keep a flow maintained until a new solution container or bag 11 can be utilized. In the event a new solution container is not interconnected to set 10 before all liquid empties from chamber 20, a level of liquid will be maintained in sight chamber 12 as filters 38 and 40 will afford an air lock. A new venipuncture will not be required because of the hydrostatic pressure. All that is required is to connect a new solution container 11 and reprime reservoir 20 as previously indicated.

The length of time that the KVO rate is delivered after the container 11 empties is dependent on the volume of solution in the reservoir chamber 20 and the rate of flow that the lower membrane 40 allows liquid to pass. Controlled I.V. administration apparatus 10 when utilizing the previously described cellulose acetate filters for filter means 40 was effective under the following conditions:

TABLE I

| Range of Administration Flow Rates Regulated by Flow Control Device (15) | Run | |
|---|---|---|
| | No. 1 | No. 2 |
| Flow Rate Range | 0–66 ml./min. | 0–60 ml./min. |
| KVO Flow Rate | 4 ml./hr. | 9–10 ml./hr. |
| KVO Time Length | 2½ hrs. | 45 min. |

It will be recognized that the membrane filter 40 is selected such that it restricts the flow of remaining fluid 16 by using a controlled porosity, consistent flow characteristics, and a calibrated cross-sectional flow area. The KVO rate is independent of the flow rate set by clamp 15 provided the flow clamp is adjusted to a faster rate than the KVO rate. Because of the porosity and hydrophilicity of membrane 40, it will not pass air when the reservoir 20 empties.

The operation of embodiments 110 and 610 will be the same as previously indicated for unit 10 except that the flow through the smaller second orifices 136 and 636 will be effected for accomplishing the KVO rate when the liquid level falls below the upper filters 138 and 638. The sole flow is through channels 137 and 637 forming the second orifices 136 and 636. These units have the disadvantage that the second orifices 136 and 636 do not have a filter to exclude air and particulate matter.

Unit 210 will afford the same function as the previous units and exactly the same as in unit 10 through the use of the double filter system afforded by filters 238 and 240, except air will be vented into a rigid-walled solution container by means of the combined filter and check valve assembly 257.

The same KVO flow rate to afford time for replenishing the source of solution will be effected by means of embodiments 310, 410 and 510. The basic difference between these and the previous embodiments is that the upper orifices 333, 433 and 533 will be sealed from any incoming air in the reservoirs by float valves 350, 450 and 550 as the respective float valves are drawn down with the liquid and seated on the respective orifices defined by an annularly, pointed ridge 349, 449 and 549. The operations of the second orifices 336, 436 and 536, which are constructed to deliver a slower rate of liquid, will then come into effect as the liquid level drops below the surface of the upper orifices.

Unit 710 while resembling administration apparatus 10 in the use of a double filter system, employs the filters in an adjacent and concentric arrangement. A further distinction is in utilizing the first orifice 733 with filter means 738 outside tubular member 730 whereas the second orifice with the KVO filter 740 is placed inside the central fluid passage means 730. During operation, the liquid level in the tubular passage means will be at its upper limits as indicated by numeral 770 as a slower flow rate is effected across filter 740. At the outside of tubular member 730 and the portion forming orifice chamber 774, the liquid level will be approximately midway as indicated by numeral 771 as the flow rate across filter 738 is faster. When the liquid in container 11 empties, liquid level 771 will continue to diminish at a predetermined rate until the liquid in chamber 774 is exhausted. At this stage the liquid in tubular passage means 730 will still be substantially at its upper level so that tubular passage means acts as a reservoir for liquid to pass through filter 740 at the slower rate to effect the KVO principle. Consequently, in this embodiment, tubular member 730 acts as a KVO reservoir. This unit as is true of units 10, 210 and 510, have the advantage of retaining liquid in the delivery tube 714 even when the supply of liquid in 720 is exhausted. This is accomplished by the air lock provided by KVO filters 40, 240, 540 and 740.

The foregoing described units are all disposable with the respective reservoir chambers 20, 120, 220, 320, 420, 520, 620 and 720 formed from a clear flexible plastic cellulose propionate material. The cylindrical walls are solvent sealed to the piercing pin assemblies as well as to the end closures. The same technique is employed in securing the drip chambers to the annular flanges in the outlet closures. In those units which employ the filtering means, the filters are secured to the fluid passage means by a heat seal with the fluid passage means or the horn being composed of a rigid ABS (acrylonitrile/butadiene/styrene) material. Obviously, other plastic materials could be employed which are inert to I.V. liquids and in the instance of the side walls 21 it could be composed of glass although this would pose a slightly more difficult problem in priming the system. In the embodiment shown in FIGS. 5-7, the float valve with the diaphragms are composed of a rubber material as well as the hinging arms and the retaining member around the diaphragm. While cellulose acetate is the preferred material for composing the filters used in this certain embodiment, other filtering materials of the cellulose family or derivatives of the cellulose family such as cellulose nitrate, cellulose triacetate, mixed esters of cellulose or regenerated cellulose could be employed with the provision that they be hydrophilic with a maximum pore size of less than 10 micrometers. Filters made from vinyls, copolymers of vinyls and polycarbonate could also be used.

It will thus be seen that through the present invention there is provided a controlled I.V. administration apparatus which is simple in its construction yet will allow for a reduced but continuous flow rate of fluid automatically after a fluid level drops below a predetermined level. Except for vertical placement, no special orientation is required. In those instances where filter materials are employed across the various orifices, added advantages are obtained in that a filtering of any particulate material is effected, the elimination of any flow of gas into the system and elimination of a new venipuncture even when the liquid in the reservoir chamber is completely exhausted. The administration apparatus of this invention can be composed of inexpensive materials and thus is disposable. Automatic reversion from a faster flow rate to a slower flow rate is accomplished without supervision of the units and without a source of external power.

The foregoing invention can now be practiced by those skilled in the art. Such skilled persons will know that the invention is not necessarily restricted to the particular embodiments presented herein. The scope of the invention is to be defined by the terms of the following claims as given meaning by the preceding description.

I claim:

1. An apparatus for administering a parenteral liquid from a parenteral liquid container to the patient comprising:
   a reservoir chamber;
   connection means for said fluid container in fluid-tight engagement with one end of said chamber, said connection means defining a fluid flow inlet passageway into said chamber;
   means defining a closure for another end of said chamber, said closure means providing for a fluid flow outlet passageway;
   fluid passage means extending into said chamber and in communication with said fluid flow inlet and outlet passageways;
   means disposed in said chamber defining a first and a second orifice in communication with said fluid flow outlet passageway with at least one of said orifices communicating with said fluid passage means, said first and second orifices spaced from each other a predetermined distance and separately communicating with said outlet passageway;
   means operatively associated with said first and second orifices and within said reservoir chamber to provide a reservoir of said liquid for flow through said second orifice after flow of said liquid through said first orifice and to substantially eliminate the flow of air into said first orifice; and
   means operatively associated with said outlet passageway for administering said liquid.

2. The apparatus as defined in claim 1 wherein said connection means defining said fluid flow inlet passageway comprises a hollow piercing pin.

3. The apparatus as defined in claim 2 wherein said piercing pin includes an additional passageway to provide entry of air into said container.

4. The apparatus as defined in claim 2 wherein said means for administering said liquid associated with said outlet passageway includes a drip forming member and said apparatus further includes a flexible drip chamber surrounding said drip forming member with a length of tubing secured to said drip chamber and a flow control means operatively associated with said tubing.

5. The apparatus as defined in claim 1 wherein said first orifice has a larger opening than said second orifice.

6. The apparatus as defined in claim 1 wherein said means operatively associated with said first and second orifices to provide a reservoir of said liquid for flow through said second orifice after flow of said liquid through said first orifice comprises in part filter means extending over at least said first orifice.

7. The apparatus as defined in claim 6 wherein said filter means are operatively associated with both said first and second orifices.

8. The apparatus as defined in claim 7 wherein said filter means associated with said first orifice is of a larger mesh size than the filter means associated with said second orifice.

9. The apparatus as defined in claim 7 wherein said filter means is of the hydrophilic type.

10. The apparatus as defined in claim 7 wherein said orifices are defined by a substantially flat wall at the mouth of each orifice and each said filter means is substantially flat and secured to said flat wall.

11. The apparatus as defined in claim 6 wherein said filter means is composed of cellulose acetate material.

12. An apparatus for administering a parenteral liquid from a parenteral liquid container to the patient comprising:
   a reservoir chamber;
   connection means for said fluid container in fluid-tight engagement with one end of said chamber, said connection means defining a fluid flow inlet passageway into said chamber;
   closure means in fluid-tight engagement with another end of said chamber, said closure means defining a fluid flow outlet passageway;
   fluid passage means extending into said chamber and in communication with said fluid flow inlet and outlet passageways;
   means defining a first and a second orifice in separate communication with said fluid passage means, said first and second orifices spaced from each other a predetermined distance, said first orifice positioned a greater distance inwardly in said chamber and away from said closure means defining said outlet passageway;
   means operatively associated with said first and second orifices and within said reservoir chamber to provide a reservoir of said liquid for flow through said second orifice after flow of said liquid through said first orifice and to substantially eliminate the flow of air into said first orifice; and
   means connected to said closure means defining said outlet passage for administering said liquid.

13. The apparatus as defined in claim 12 wherein said fluid passage means comprises an elongated tubular member with one end forming said first orifice and an opposing end comprising said drip forming member with a length of tubing secured to said drip chamber and a flow control means operatively associated with said tubing.

14. The apparatus as defined in claim 13 wherein said second orifice is defined by a tubular member extending laterally from said elongated tubular member and said first orifice is defined by an enlarged diameter section.

15. The apparatus as defined in claim 14 wherein said tubular member comprising said second orifice extends within the confines of said first orifice if extended.

16. The apparatus as defined in claim 13 wherein said elongated tubular member is formed in two separate portions and said second orifice is defined by an opening between said two portions and a capillary-like opening in the wall surface of one of said portions.

17. The apparatus as defined in claim 12 wherein said means to substantially eliminate the flow of air into said first orifice is a float valve operatively secured to said fluid passage means to effect a closing of said first orifice when the fluid level is below said frist orifice.

18. The apparatus as defined in claim 17 wherein said second orifice is defined by a calibrated opening.

19. The apparatus as defined in claim 17 wherein said second orifice is defined by a calibrated valve member.

20. The apparatus as defined in claim 17 wherein said second orifice has filter means secured thereto and covering said second orifice.

21. The apparatus as defined in claim 17 wherein said float valve is of the diaphragm type with an arm member extending therefrom and said fluid passage means comprises an extending portion adjacent said first orifice for pivotal attachment with said arm of said float valve.

22. The apparatus as defined in claim 4 wherein both said reservoir chamber and said drip chamber are composed of a transparent, flexible plastic material and said fluid passage means is composed of rigid plastic material.

23. An apparatus for administering a parenteral liquid from a parenteral liquid container to the patient comprising:
   a reservoir chamber;
   connection means for said fluid container in fluid-tight engagement with one end of said chamber, said connection means defining a fluid flow inlet passageway into said chamber;
   closure means in fluid-tight engagement with another end of said chamber, said closure means defining a fluid flow outlet passageway;
   fluid passage means extending into said chamber and in communication with said fluid flow inlet and outlet passageways;
   means defining an orifice in communication with said fluid passage means and said fluid flow inlet and outlet passageways;
   means defining another orifice in separate communication with said fluid flow inlet and outlet passageways, said other orifice spaced from said fluid passage means and said orifice in communication with said fluid passage means;
   means operatively associated with both said orifices and within said reservoir chamber to provide a reservoir of said liquid for flow through said orifice in communication with said fluid passage means after flow of said liquid through said other orifice and to substantially eliminate the flow of air into said other orifice; and
   means connected to said closure means defining said outlet passage for administering said liquid.

24. The apparatus as defined in claim 23 wherein said fluid passage means is defined by an open ended tubular member.

25. The apparatus as defined in claim 24 wherein said tubular member is substantially centrally positioned in said reservoir chamber and in alignment with said fluid flow inlet and outlet passageways.

26. The apparatus as defined in claim 25 wherein said orifice in communication with said tubular member is disposed at the end opposite its open end and said other orifice is spaced outside the confines of said tubular member and concentrically positioned with respect thereto.

27. The apparatus as defined in claim 26 wherein said means operatively associated with both said orifices to provide a reservoir of said liquid for flow through said orifice in communication with said tubular member comprise in part filter means extending over both said orifices.

28. An automatic flow regulator for delivering a fluid, such as a parenteral solution, from a source to a patient, the flow regulator comprising: a reservoir chamber for receiving fluid from the source; inlet means at one end of said reservoir chamber for associating with said source, and for delivering fluid from said source to said reservoir chamber; outlet means at the opposite end of said reservoir chamber for delivering fluid from said reservoir chamber to the patient; primary delivery means for conveying fluid from said reservoir chamber to said outlet means at a first flow rate; valve means positioned within said reservoir chamber and in the fluid path between said reservoir chamber and said primary delivery means, said valve means being for discontinuing the conveyance of fluid from said reservoir chamber to said outlet means and for preventing the passage of air through said primary delivery means when the level of fluid in said reservoir chamber drops, by continued infusion, below a predetermined threshold level; and secondary delivery means for continually conveying fluid from said reservoir chamber to said outlet means at a second flow rate less than said first flow rate, whereby the flow of fluid to said outlet means is from said primary delivery means and said secondary delivery means when the level of fluid is above said threshold level, but is only from said secondary delivery means when the level of fluid is below said threshold level.

29. An automatic flow regulator for delivering a fluid, such as a parenteral solution, from a source to a patient, the flow regulator comprising: a reservoir chamber for receiving fluid from the source; inlet means at one end of said reservoir chamber for associating with said source, and for delivering fluid from said source to said reservoir chamber; outlet means at the opposite end of said reservoir chamber for delivering fluid from said reservoir chamber to the patient; primary delivery means for conveying fluid from said reservoir chamber to said outlet means at a first flow rate, said primary delivery means including a mechanism for discontinuing the conveyance of fluid from said reservoir chamber to said outlet means when the level of fluid in said reservoir chamber drops, by continued infusion, below a predetermined threshold level; secondary delivery means for continually conveying fluid from said reservoir chamber to said outlet means at a second flow rate less than said first flow rate; wherein said mechanism includes valve means which closes to the passage of air when said level of fluid drops below said threshold level.

30. The flow regulator recited in claim 29 wherein said valve means is a float valve.

31. The flow regulator recited in claim 29 wherein said valve means is a membrane designed to pass fluid, but to block the flow of air.

* * * * *